United States Patent [19]
Gorman, Jr.

[11] Patent Number: 5,191,211
[45] Date of Patent: Mar. 2, 1993

[54] THERMAL DESORPTION METHOD FOR SEPARATING VOLATILE ADDITIVES FROM VULCANIZABLE RUBBER

[75] Inventor: William B. Gorman, Jr., Mooresville, Ind.

[73] Assignee: Bridgestone/Firestone, Inc., Akron, Ohio

[21] Appl. No.: 856,263

[22] Filed: Mar. 23, 1992

[51] Int. Cl.[5] ............................................. B01D 59/44
[52] U.S. Cl. .................................. 250/282; 250/288; 73/23.35; 73/23.41
[58] Field of Search ................. 250/282, 281, 288 R, 250/288 A; 73/23.37, 23.35, 23.41, 23.25, 23.39

[56] References Cited
U.S. PATENT DOCUMENTS

| | | | |
|---|---|---|---|
| 3,715,910 | 2/1973 | Fore et al. ........................... | 73/23.25 |
| 3,768,302 | 10/1973 | Barringer ........................... | 73/28.01 |
| 4,004,881 | 1/1977 | Ligon, Jr. ........................... | 73/23.35 |
| 4,035,168 | 7/1977 | Jennings ............................. | 73/23.35 |
| 4,159,894 | 7/1979 | Hu ..................................... | 73/23.41 |
| 5,027,643 | 7/1991 | Jenkins ............................... | 73/23.39 |

Primary Examiner—Constantine Hannaher
Assistant Examiner—Kiet T. Nguyen
Attorney, Agent, or Firm—Frank J. Troy, Sr.

[57] ABSTRACT

Volatile additives for vulcanized or unvulcanized rubber can be accurately identified by controlled heating of a test sample in a sealed vial equipped with an overhead collecting headspace, transferring the heated volatiles to a chromatograph column, and analyzing the separated volatile components emerging from the chromatograph column by various selective analytical detectors.

12 Claims, 6 Drawing Sheets

Electron Impact (70ev) Mass Spectrum of Additives in a Rubber Vulcanizate (Direct Analysis)

THERMAL DESORPTION METHOD FOR SEPARATING VOLATILE ADDITIVES FROM VULCANIZABLE RUBBER

FIELD OF THE INVENTION

This invention pertains to separating volatile additives from vulcanizable rubber and more particularly to an analytical method of separating and identifying volatile additives for vulcanized or unvulcanized rubber compounds.

BACKGROUND

Classical analysis of polymeric compounds such as rubber compounds for identification of additives such as accelerators, antioxidants, and antiozonants require a very difficult separation step of such additives from the rubber compound prior to analysis. Thermosetting polymers such as vulcanized rubber are even more difficult to analyze than thermoplastic polymers due to the compounding ingredients being locked into the matrix by carbon black and crosslinking of the rubber polymer. The classical method for separating volatile additives from rubber is by solvent extraction. Modern separation techniques such as thermogravimetric analysis (TGA) or pyrolysis will produce volatile fragments of additives, but these modern separation techniques are quite complex and result in incomplete analysis due to poor resolution and the inability to separate oligomers of polymer and oil. A further problem inherent in most thermosetting rubber mixtures evolves from many of the additives being already fragmented due to the curing and crosslinking process. Existing extraction techniques produce fragments while the modern thermal methods produce highly fragmented products as well as create interferences from the polymers and organic softeners. Desorption methods such as TGA cause further fragmentation of the fragmented additives thereby preventing recovery of the original fragments.

A current prior art method of analyzing additives to vulcanized rubber compounds involves direct insertion of the vulcanized rubber into an ion source of a mass spectrometer, but this does not allow for the selective separation of process oils or volatile fragments, and further produces a complex spectrum containing ion fragmentation of the entire compound. Limitations on the small sample size render it difficult to detect the typical low concentrations of volatile additives in conventional rubber compounds. A further problem of the direct insertion method relates to inefficient extraction and isolation of the organic additives from the inorganic additives primarily due to carbon black matrices. The direct insertion method typically requires frequent and costly maintenance of equipment due to the deposition of large amounts of non-volatile material on the ion source.

SUMMARY OF THE INVENTION

Briefly, this invention pertains to a process for separating volatile components such as accelerator fragments, antioxidants and other organic additives from vulcanized rubber or unvulcanized rubber for the purpose of analytically analyzing the separated volatile compounds. The separation process comprises the steps of sealing the test sample of vulcanizate in a sealed glass vial containing a controlled atmosphere and having an overhead headspace, heating the test sample in the vial to a predetermined temperature and for time sufficient for complete desorption and volatization of volatile components into gas which collect in the vial headspace while other less volatile additives remain in the vial as a liquid or solid along with solid unpyrolized test sample. The volatile gasses are maintained as gasses and transferred to a separation means such as a gas chromatography column for separation of the volatile components which are transferred to an analytical detector for specific identification of the recovered volatile components.

A surprising advantage of the process of this invention is that the volatilization step can utilize directly a sample of vulcanized rubber without the conventional prior sample preparation such as milling, extraction or pyrolysis. For instance, this process allows the thermal desorption and concentration of volatiles from test samples having a weight up to about 10 grams without prior test sample preparation. Sample size, temperature, and heating time can be varied to allow optimal concentration of volatiles necessary for analytical detection and identification. These and other advantages will become more apparent by referring to the detailed description of the invention and the illustrative example.

DETAILED DESCRIPTION OF THE INVENTION

Figure 1:
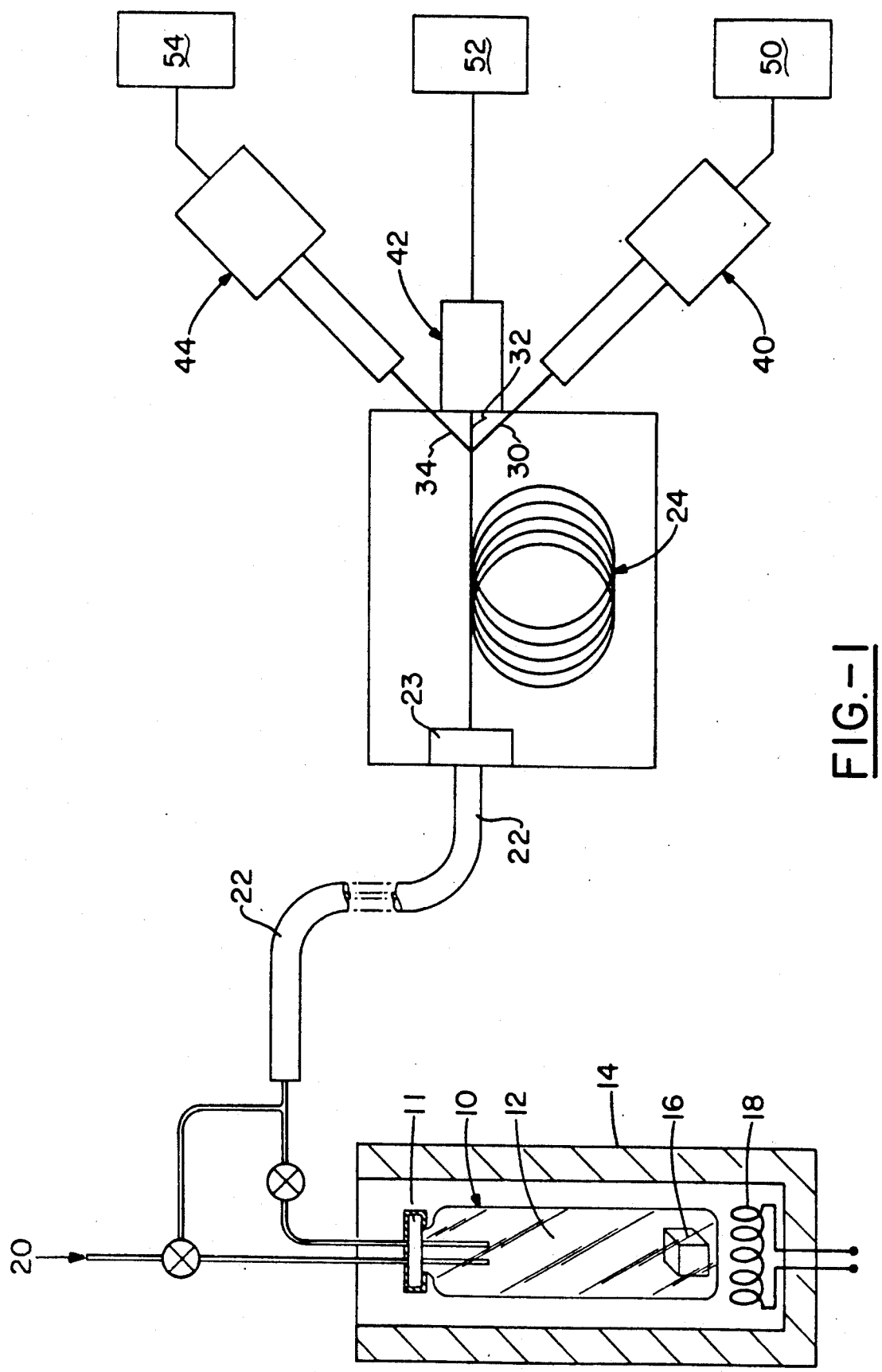
FIG. 1 is a schematic drawing of the process of this invention disclosing a sealed glass vial.

The process of this invention is directed to separating volatile additive components, such as accelerator fragments, antioxidants, and other organic additives, from vulcanized or unvulcanized rubber compounds by controlled thermal desorption to selectively separate the volatile components. A glass vial 10, sealed with a teflon faced septa seal 11, comprising an overhead glass headspace 12 communicating with a bottom heating section 14 containing a test strip sample 16 adapted to be heated by a controlled heat source 18. The vial 10 is fitted with an external dilution or carrier gas source 20 and with an overhead fused silica transfer line 22 adapted to be heated and operatively interconnected to a capillary chromatography column 24 fitted with a plurality of restrictors and stream splitters shown as three restrictive connectors 30, 32, 34 where each connector 30, 32, 34 is individually interconnected to a gas analyzer detector 40, 42, 44, respectively. Each analyzer detector 40, 42, 44 can be a mass spectrometer, a flame ionization detector, a Fourier Transform infrared spectrometer, or compatible gas analyzer detector means which are interfaced with integrators, data stations and/or computers (50, 52, 54) for data storage and library reference comparisons.

A small test sample from about 2 grams up to about 10 grams in weight is placed in a sealed test vial for thermal desorption and analysis. Preferred test sample sizes are from about 4 grams to 6 grams. The test sample of vulcanized or unvulcanized rubber is placed in glass vials equipped with an overhead headspace and sealed under a controlled atmosphere within the vial by a teflon septa seal on the vial opening. The vial is then heated under controlled temperatures for time sufficient to completely volatilize the volatile components of interest which enter and collect in the overhead headspace as gasses while less volatile components such as process oils remain in the vial as a liquid or solids. Heating at the proper temperature for a selected time efficiently enables concentration of the volatile gasses in the headspace and desorption of such volatile gasses from the test sample to reach equilibrium. The test sample is heated to a temperature at least 150° C. and not above 230° C., and preferably between 190° C. and 200° C. The test sample is heated for time sufficient for complete desorption of the test sample and typically for about 1 to 4 hours. Preferred heating conditions comprise heating between 190° C. and 200° C. for about one hour. Pressures inside the vial are normally atmospheric or near atmospheric. Hence, thermal desorption can be effectively controlled to volatilize components such as accelerator fragments and antioxidants or other desired volatiles into the overhead headspace while process oil and other less volatile components are maintained in the vial. Polymer pyrolysis and fragmentation of the volatiles are effectively avoided in the heating step and non-volatiles left in the vial can be easily discarded.

In accordance with the process of this invention, the headspace vial contains the volatile gasses collected by placing the vial in a suitably heated injection receptacle or the vial is heated externally to maintain the vial above the temperature required to maintain the volatile components in a gaseous state and to avoid condensation into liquid. Preferred minimum temperature is at least above 120° C. and preferably above 150° C. The vial is pressurized mildly with a fixed volume of a carrier gas comprising an inert gas such as helium or a reactive gas such as oxygen or ammonia, but at a pressure below about 30 psi to avoid undesirable failure of the seal and venting of the volatilized components. The volatilized gasses along with the carrier gas are swept from the vial in a fixed volume and transferred to the capillary column 24 by a heated transfer means such as a fused silica transfer line 22. The gasses from the headspace are separated on a thick film capillary column 24 using cryogenic cooling 23 if necessary to improve resolution. The volatile gasses are injected into a capillary chromatography column through the transfer line from the vial to effect separation of the volatile components for sequential introduction into a detector system such as a mass spectrometer, a flame ionization detector, or an infrared spectrometer. Hence, the chromatography column effluent can be split into two or three streams regulated by restrictors and enter either the mass spectrometer interface, the flame ionization detector, and/or an FTIR transfer line as by using a suitable deactivated column splitter. The various analyzing means provide accurate data for the identification of volatile components, including volatile fragments such as accelerator fragments, free of interfering fragments such as are produced using prior techniques. The identified volatile components can be compared with similar but known vulcanizates under varying atmospheres, temperatures and age conditions of the test sample to accurately identify the volatiles form the test sample.

Figure 2:
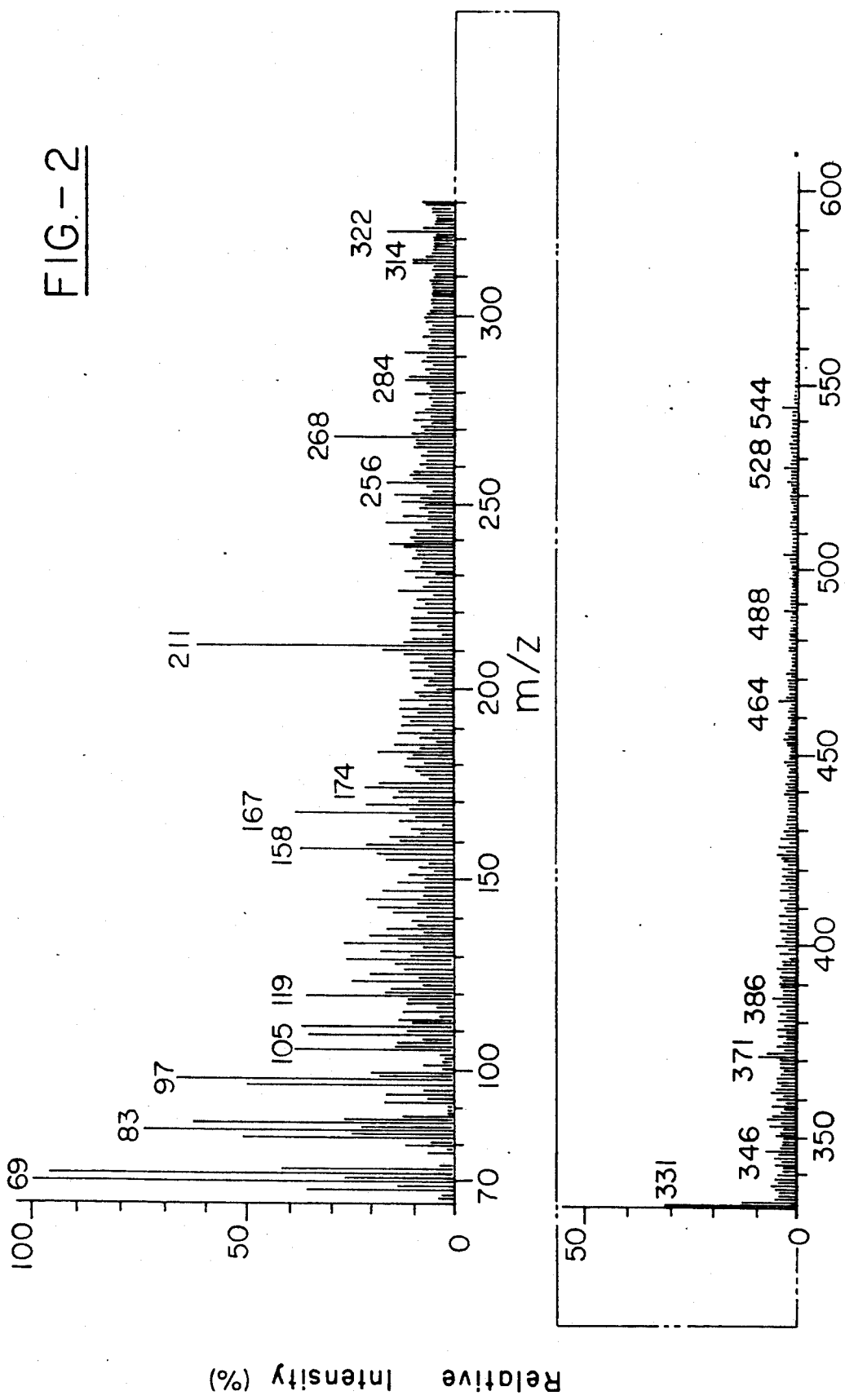
FIG. 2 is a mass spectrogram for a vulcanizate inserted directly into the ion source of a mass spectrometer.

The advantages of the present invention are illustrated in FIGS. 2–10, which compare a known method for identifying additives in a rubber vulcanizate to the method of the present invention. FIG. 2 is a mass spectrogram for a vulcanizate inserted directly into the ion source of a mass spectrometer in accordance with the prior art. No separation of components occurs with this method. The resulting mass spectrogram for such a mixture is extremely complex and difficult to interpret because many of the components will generate fragments having molecular weights similar to those of other components.

Figure 3:
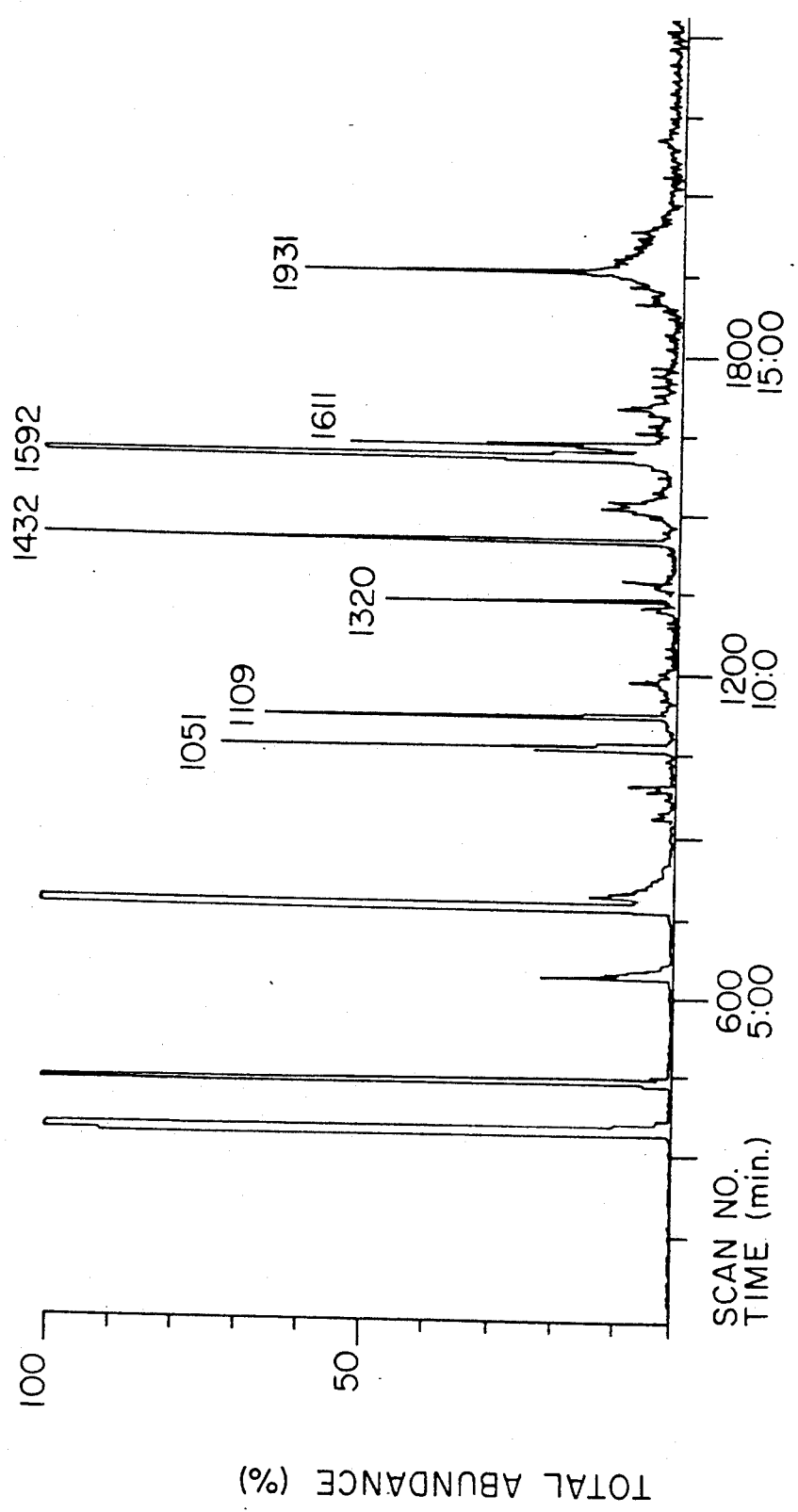
FIG. 3 is a chromatograph for a vulcanizate similar to that used to generate the spectrogram in FIG. 2.
Figure 4:
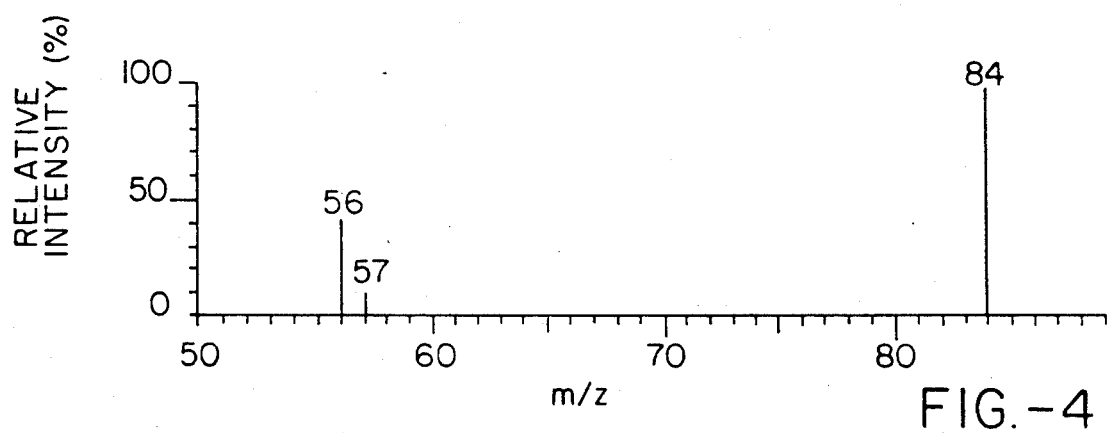
FIGS. 4 through 10 are mass spectrograms for the individual components which generated the peaks designated 4 through 10, respectively, in FIG. 3.
Figure 5:
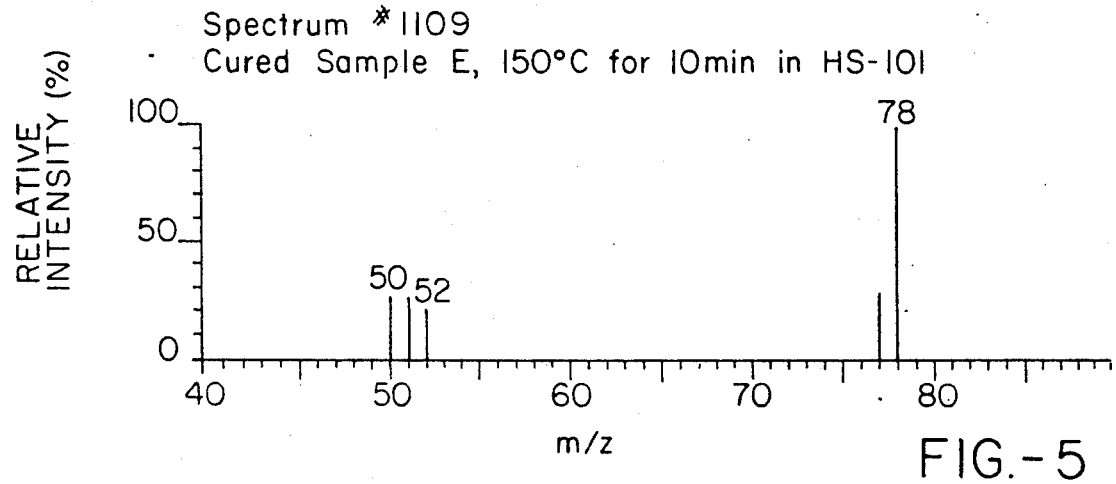
Figure 6:
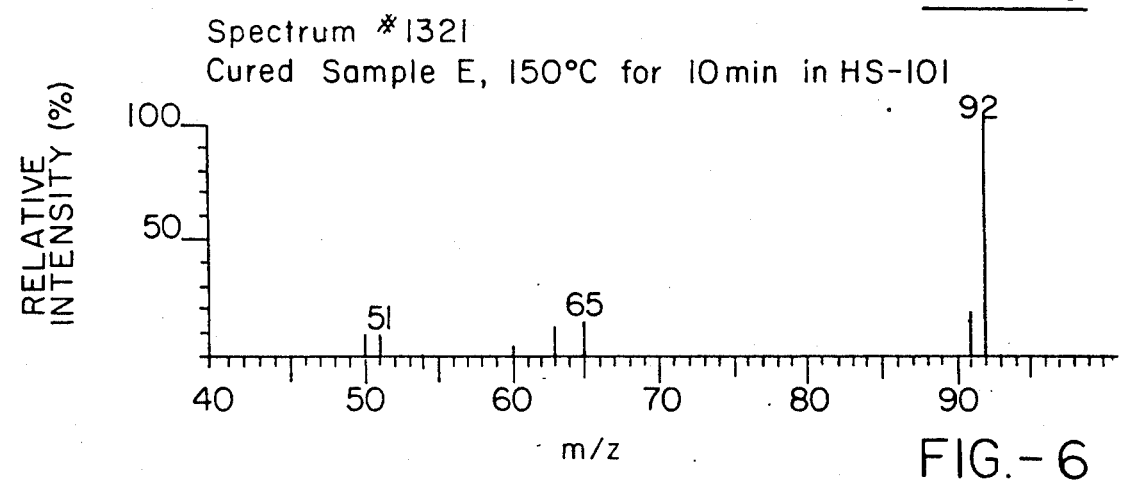
Figure 7:
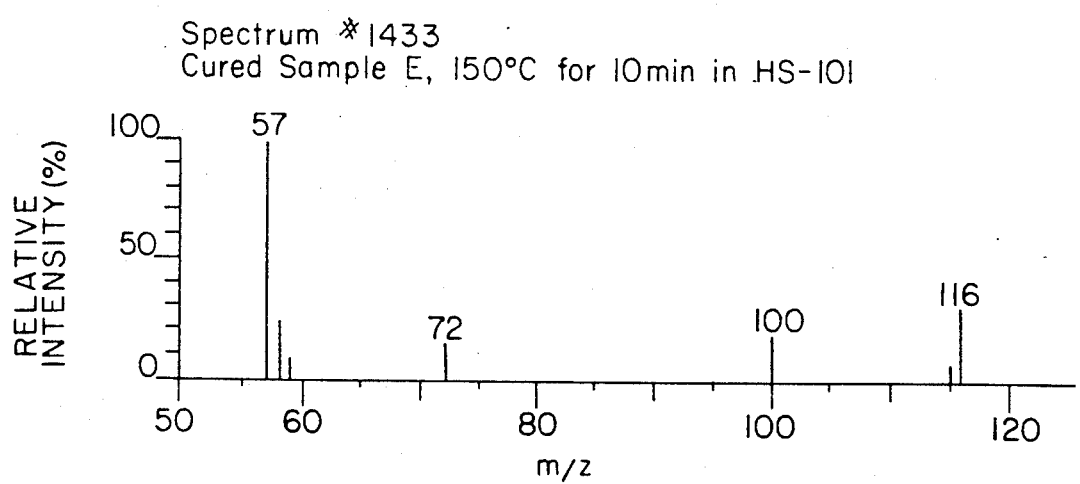
Figure 8:
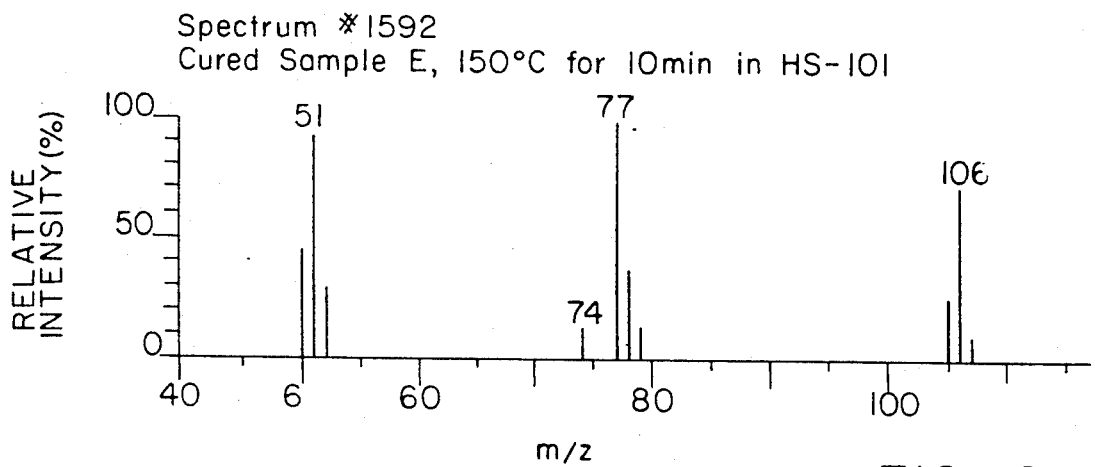
Figure 9:
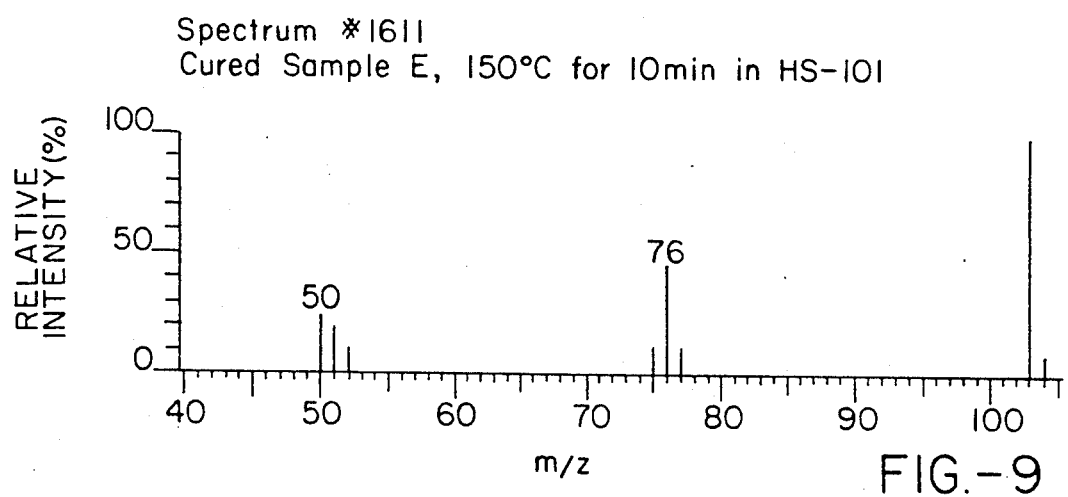
Figure 10:
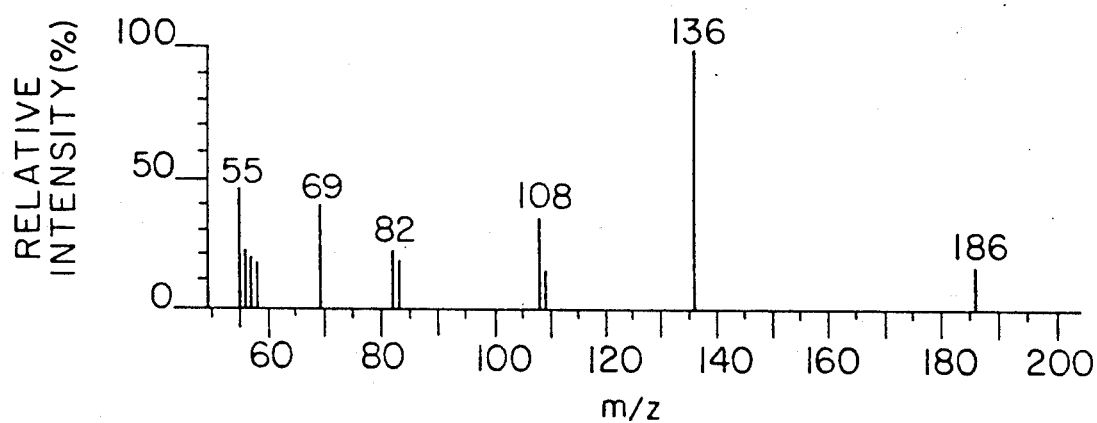

The separation of components in the gas chromatography column for a compounded rubber, similar to the one used to generate the spectrogram in FIG. 2, is shown in FIG. 3. The various peaks represent the individual components which exit the column sequentially.

FIGS. 4–10, which represent data obtained by the method of the invention, are mass spectrograms for the individual components which generated the peaks designated 4–10 respectively in FIG. 3. These mass spectrograms are each unique to an individual component, and are consequently much easier to interpret.

ILLUSTRATIVE EXAMPLE

In accordance with a preferred embodiment of the process of this invention, a 4 to 5 gram test sample 16 of vulcanized or unvulcanized rubber material is placed inside a 20 to 30 ml. sealed glass test vial 10. The test sample 16 can be cut into narrow strips to increase the surface area of the test sample 16 to shorten the desorption time. The glass vial 10 is purged with either an inert gas or some known reactive gas atmosphere and then sealed tightly with a teflon septum seal to contain the volatile gasses in the headspace of the vial. The vial 10 is then heated to about 190° C. for time sufficient to completely desorp the gaseous volatile components from the test sample 16 which ordinarily takes from about 1 to 2 hours. After the desorption step is completed, the vial 10 is placed into the headspace sampler and allowed to equilibrate the temperature in the headspace 12 at about 150° C. for about 5 to 10 minutes. The vial 10 is pressurized slightly with an inert carrier gas such as helium. About 0.2 to 0.4 ml. of volatile gasses collected in the headspace 12 is metered into the carrier gas which is transferred to the chromatography column 24 by a heated fused silica transfer line 22. Within the chromatography column 24, the volatile components are separated on a thick film, non-polar stationary phase in a 0.53 mm I.D. fused silica capillary column 24 using cryogenic focusing and temperature control. The volatile components, which enter the capillary column as a mixture, pass through the column at different rates so that the components exit sequentially over discrete time ranges. The capillary column is terminated with at least one 0.1 mm I.D. fused silica restrictor 30 about 10 cm. long. The restrictor 30 is interconnected to an analyzer 40 which can be a mass spectrometer or a flame ionization detector, an infrared spectrometer or similar analyzer detector, as desired. The effluent gas from the capillary column 24 can be analyzed by a plurality of analyzer detectors 40, 42, 44 simultaneously to attain additional analytical information. The resultant identification of volatile components can be compared with volatiles recovered from known vulcanizates under varying atmospheres, temperatures, and age conditions of the test sample. The resultant spectra obtained from the analyzer detectors will be clean of interferences and more readily interpretable. The non-volatiles remain in the bottom of the vial 10 and can be discarded with the vial.

The process of this invention provides controlled thermal desorption of a test sample without contamination with process oil and polymer pyrolysis while volatile components, including volatile fragments, are not further fragmented due to excessive heat and can be accurately analyzed. The process further provides for accurate study of volatile additives under inert and reactive gas atmospheres. Test sample size, temperatures and heat times can be varied as desired to allow desirable concentration of volatiles and to provide accurate detection and identification.

While in accordance with the Patent Statutes, the best mode and preferred embodiment has been set forth, the scope of the invention is not limited thereto, but rather by the scope of the attached claims.

What is claimed is:

1. A process for separating and identifying volatile components from a test sample of vulcanized or unvulcanized rubber compound, comprising the steps of:
   a) heating the test sample in a sealed vial having an overhead collecting headspace at temperature sufficiently high to volatilize the volatile components in the test sample but below a pyrolysis temperature of the polymer to avoid pyrolysis of the test sample;
   b) allowing the volatile components to collect in the headspace;
   c) transferring the volatile components at a temperature sufficient to maintain the gaseous state of the volatile components, to a chromatograph column to separate the volatile components; and
   d) transferring each component to an analyzer detector for identification.

2. The process of claim 1, wherein the test sample in the vial is heated to a temperature between about 150° C. and 230° C.

3. The process of claim 1, wherein the volatile components collected in the headspace of the vial are diluted with a carrier gas prior to transfer to the chromatography column.

4. The process of claim 3, wherein the carrier gas is a measured volume of inert gas.

5. The process of claim 3, wherein the carrier gas is a measured volume of a known reactive gas atmosphere.

6. The process of claim 3, wherein the carrier gas and volatile compounds are equalized at a temperature between about 145° C. and 155° C. prior to entering the chromatography column.

7. The process of claim 6, wherein the volatile components are heated to a temperature between about 120° C. and 190° C. while transferring the volatile components to the chromatography column.

8. The process of claim 1, wherein the volatile components include accelerate fragments.

9. The process of claim 1, wherein the volatile components are each analyzed by an analyzing detector comprising a mass spectrometer.

10. The process of claim 1, wherein the volatile components are each analyzed by flame ionization.

11. The process of claim 1, wherein the volatile components are each analyzed by an infrared spectrometer.

12. The process of claim 1, wherein the analyzer detector is a mass spectrometer, a flame ionization spectrometer, or a Fourier Transform infrared spectrometer.

* * * * *